United States Patent [19]

Giammatteo et al.

[11] Patent Number: 5,265,635
[45] Date of Patent: Nov. 30, 1993

[54] CONTROL MEANS AND METHOD FOR CONTROLLING FEED GASES

[75] Inventors: Paul J. Giammatteo, Southbury, Conn.; Richard J. Trocino, Poughkeepsie; Gregory Marsh, Newburgh, both of N.Y.

[73] Assignee: Texaco Inc., White Plains, N.Y.

[21] Appl. No.: 960,323

[22] Filed: Oct. 13, 1992

[51] Int. Cl.$^5$ ............................................. G05D 11/02
[52] U.S. Cl. ............................................. 137/3; 137/6; 137/114
[58] Field of Search ........................ 137/3, 6, 93, 114

[56] References Cited

U.S. PATENT DOCUMENTS 4,369,803 1/1983 Furr ..................................... 137/6

Primary Examiner—Robert G. Nilson
Attorney, Agent, or Firm—James J. O'Loughlin; Ronald G. Gillespie

[57] ABSTRACT

A hot feed gas is controlled by utilizing a nuclear magnetic resonance analyzer to analyze the composition of the gas and to provide at least one corresponding composition signal. A valve controls the flow of the gas in accordance with a control signal. A network connected to the analyzer and to the valve provides the control signal to the values in accordance with the composition signal so as to control the flow of the gas as a function of the composition of the gas.

16 Claims, 2 Drawing Sheets

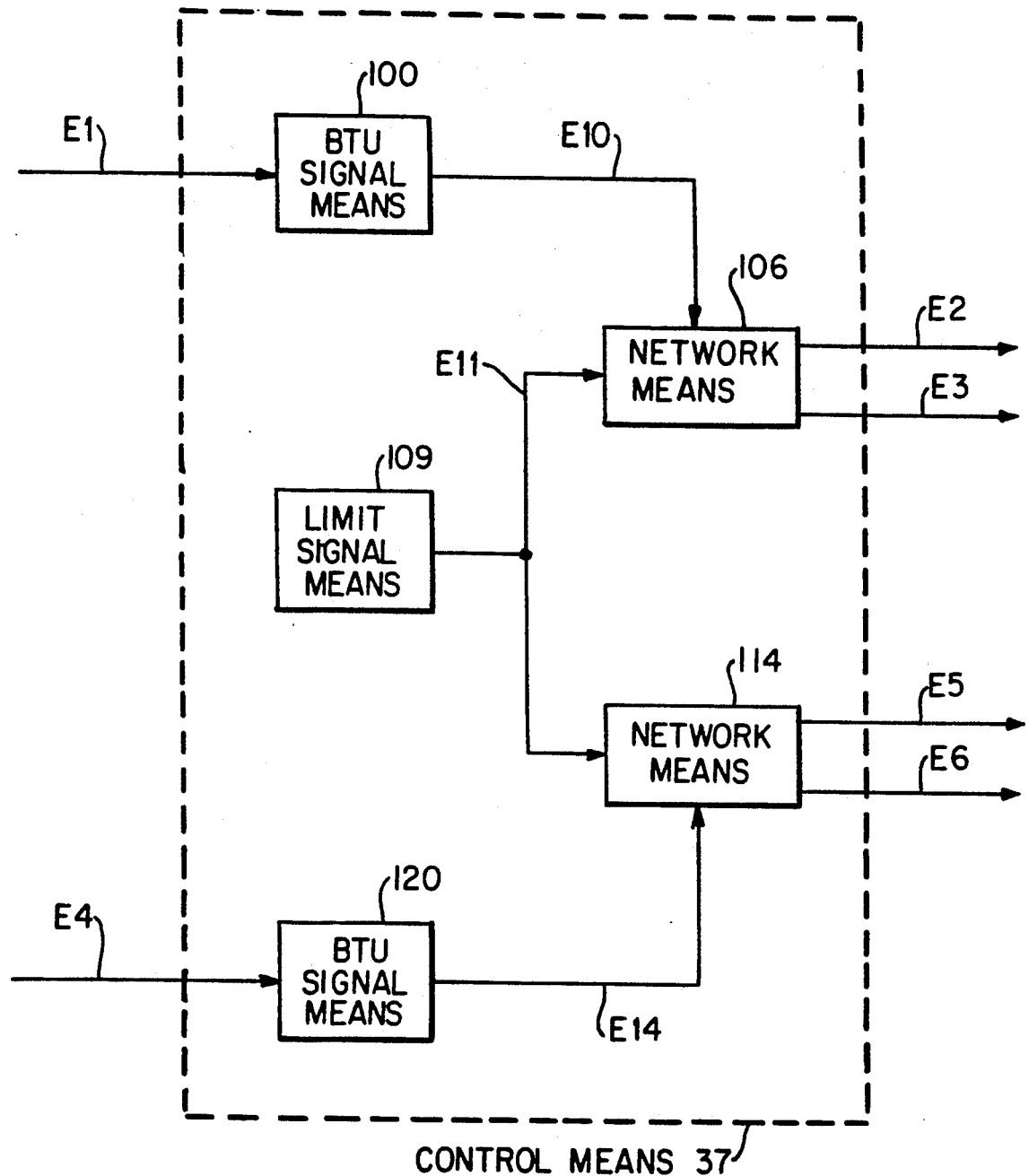

5,265,635

CONTROL MEANS AND METHOD FOR CONTROLLING FEED GASES

BACKGROUND OF THE INVENTION

1. Field of the Invention

The present invention relates to control systems and methods in general and, more particularly, to control systems and methods for controlling feed gases.

2. Summary of the Invention

A hot feed gas is controlled by utilizing a nuclear magnetic resonance analyzer to analyze the composition of the gas and to provide at least one corresponding composition signal. A valve controls the flow of the gas in accordance with a control signal. A network connected to the analyzer and to the valve provides the control signal to the values in accordance with the composition signal so as to control the flow of the gas as a function of the composition of the gas.

The objectives and advantages of the invention will appear more fully hereinafter from a consideration of the detailed description which follows, taken together with the accompanying drawing wherein one embodiment of the invention is illustrated by way of Example. It is to be especially understood, however, that the drawing is for illustration purposes only and is not to be construed as defining the limits of the invention.

DESCRIPTION OF THE DRAWING

FIG. 2 is a simplified block diagram of the control means shown in FIG. 1

DESCRIPTION OF THE INVENTION

Figure 1:
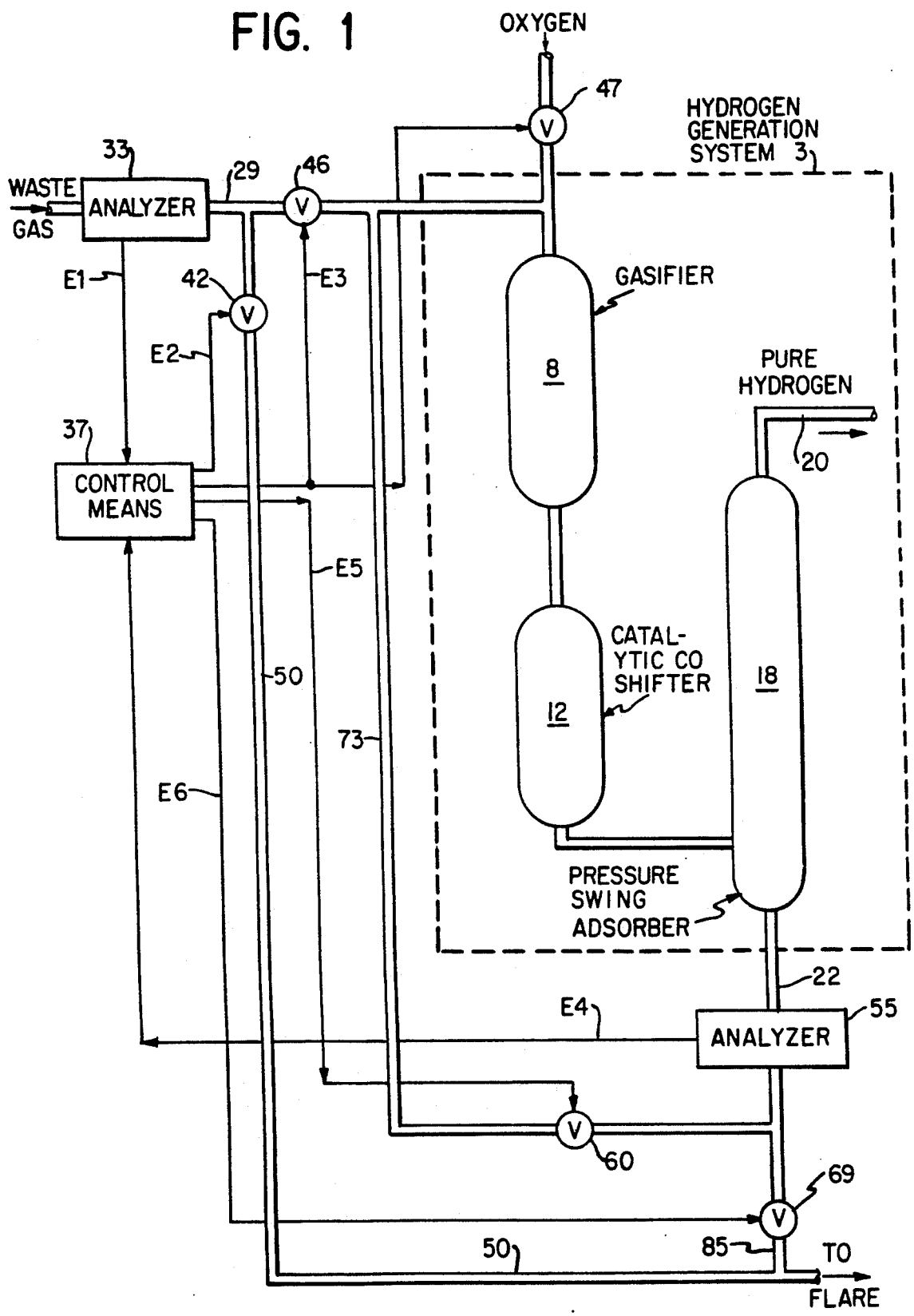
FIG. 1 is a schematic drawing of a control system, constructed in accordance with the present invention, for controlling a hydrogen generation system.

With reference to the drawing, a hydrogen generation system 3, which may be of the type described and disclosed in U.S. application Ser. No. 07/614,335, Nov. 16, 1990, now U.S. Pat. No. 5,152,976 includes a gasifier 8 receiving waste gas and oxygen as hereinafter explained. Gasifier 8 provides a gaseous output to a catalytic CO shifter 12. The output of the CO shifter 12 is provided to a pressure swing adsorber unit 18, which in turn provides pure hydrogen through a line 20 and a gas, containing unreacted hydrocarbons, through a line 22.

The present invention provides a control system by having at least one nuclear magnetic resonance (NMR) analyzer placed in the waste gas feed for the gasifier. In this regard, waste gas is provided through a line 29 which passes through NMR 33. Analyzer 33 analyzes the constituents of the waste gas and provides a corresponding signal E1 to control means 37.

Control means 37 generally will be part of the in-place control equipment in a refinery's control room with its computers and display boards showing the refinery operation. Be that as it may, control means 37 will provide signal E2 to valve 42 and signal E3 to valves 46 and 47. Valve 42 is located in a line 50 which provides gas to the flare as hereinafter explained. Valves 46 and 47 in lines 29 and 48, respectively, control the flow of the waste gas and oxygen, respectively, to gasifier 8.

Another NMR analyzer 55 analyzes the gas leaving adsorber 18 and provides a signal E4 to control means 37. Control means 37 then utilizes the analyses to provide control signals E5 and E6 to valves 60, and 69, respectively. Valve 60 is in a line 73 which controls the flow of the gas passing through analyzer 55 back into line 29 to be fed into gasifier 8. Valve 69 is in a line 85 which provides the gas from analyzer 55 to flare via lien 50.

By way of example, the waste gas may come from a Fluidic Catalytic Cracking Unit not shown. As such, the typical waste gas of such a unit may include a variety of hydrocarbons in addition to other constituents as shown in Table I.

TABLE I

| Element | Composition | Element's BTU Content | Waste Gas BTU Contribution |
|---|---|---|---|
| $H_2$ | 19.5% | 0 | 0 |
| $N_2$ | 7.4% | 0 | 0 |
| $CH_4$ | 40.5% | 836.5 BTU | 388.9 BTU |
| $C_2H_4$ | 14.4% | 1315.9 BTU | 189.5 BTU |
| $C_2H_6$ | 16.8% | 1461.9 | 245.6 BTU |
| $C_3H_6$ | 0.4% | 1945.2 | 7.8 |
| $C_3H_8$ | 600 ppm | 2088.5 | 1.3 |
| CO | 1.0% | 0 | 0 |
| $H_2S$ | 50 ppm max. | 0 | 0 |
| | | Feed Stream Total BTU: | 833.1 |

However, the NMR analyzers 33 and 55 cannot distinguish all of the elements of the gases and therefore, only provide signals corresponding to any hydrogen containing species including $H_2$, $H_2S$, $CH_4$, $C_2H_4$, $C_2H_6$, $C_3H_6$ and $C_3H_8$. The computer in control means 37 can determine the CO content from the CH's that have been monitored. As seen above, only some signals represent components having BTU value.

The BTU content of the waste gas is important to the operation of hydrogen generation system. If the BTU content of the waste gas is too low, the process may be uneconomical.

With reference to FIG. 2, there is shown control means 37 but it should be noted, as mentioned earlier, control means 37 in reality would be the computer and control apparatus that one normally finds in refinery-type operations, but for ease of explanation, a simplified block diagram is shown depicting the functions involved. In this regard, signal E1 from analyzer 33 is applied to BTU signal means 100, which derives the BTU content of the waste gas and provides signal E10, corresponding to the derived BTU content, to network means 106.

Limit signal means 109 provides limit signal E11 to network means 106 and 114. Limit signal E11 corresponds to the limit that will be placed on the BTU content as noted earlier. It should be noted that in essence, we are applying the same criteria to the off gas as we are on the waste gas. However, an operator may desire to set a different criteria and if so, there would be just a different limit signal not shown that would provide a limit reference signal to network means 114 instead of signal E1I from limit signal means 109.

In this regard, signal E4 from analyzer 55 is provided to BTU signal means 120 which in turn provide a BTU signal E14 to network means 114.

Network means 106 then determines whether the BTU content of the waste gas is within the limits defined by signal E11 and provides control signals E2 and E3 accordingly. Similarly, network means 114 determines whether the BTU content of the off gas is within the limit defined by signals E1I and provides control signals E5 and E6 accordingly.

What is claimed is:

1. A control system for controlling a first gas and a second gas provided to a processing system comprising the steps of:

first NMR means spatially arranged with the first gas being provided to the processing system for providing at least a first composition signal corresponding to the BTU content of the first gas, first valve means spatially arranged with the first gas, the second gas and the processing system for controlling the flow of the first gas and the second gas to the processing system in accordance with a control signal, and signal means connected to the first NMR means and to the first valve means for providing the control signal to the first valve means in accordance with the composition signal so as to control the flow of the first gas and the second gas as a function of the BTU content of the first gas.

2. A system as described in claim 1 in which the processing system is a hydrogen generation system, the first gas is a hot gas and the second gas is oxygen.

3. A system as described in claim 2 in which the first NMR means is means for analyzing the hot gas and providing the first composition signal corresponding thereto.

4. A system as described in claim 3 in which the signal means includes:

first BTU means for deriving the BTU content of the hot gas from the first composition signal and providing a BTU signal corresponding to the BTU content of the hot gas, first means for providing first and second limit signals corresponding to first and second predetermined BTU content limits for the hot gas, and first network means receiving the BTU content signal and the first and second limit signals for providing the control signal in accordance with the BTU content signal and the first and second limit signals.

5. A system as described in claim 4 in which the control signal provided by the signal means controls the first valve means so as to provide the hot gas and the oxygen to the hydrogen generation system when the BTU content of the hot gas is within the first and second predetermined limits and so as not to provide the hot gas and the oxygen to the hydrogen generation system when the BTU content signal is not within the first and second predetermined limits.

6. A system as described in claim 5 further comprising second valve means connected to the NMR means and to the signal means for passing the hot gas to flare or blocking the hot gas in accordance with a second control signal in a manner so that when the hot gas is not being provided to the hydrogen generation system, the hot gas is being flared.

7. A system as described in claim 1 in which the hydrogen generation system provides an off gas including unreacted hydrocarbons; and further comprises:

second NMR means for analyzing the off gas and providing a second composition signal to the signal means, and third valve means receiving the off gas from the hydrogen generation system and responsive to third and fourth control signals from the signal means for either providing the off gas back to the hydrogen generation system as a feed gas or to flare the off gas in accordance with the third and fourth control signals.

8. A system as described in claim 7 in which the signal means derives the BTU content of the off gas in accordance with the second composition signal and provides a corresponding second BTU content signal, second means for providing third and fourth limit signals corresponding to third and fourth predetermined BTU content limits, and second network means receiving the second BTU content signal for providing the third and fourth control signals to the third valve means in accordance with the second BTU content signal and the third and fourth limit signals.

9. A control method for controlling a first gas and a second gas provided to a processing system, comprising the steps of:

using first NMR means spatially arranged with the first gas being provided to the processing system to provide at least a first composition signal corresponding to the BTU content of the first gas, controlling the flow of the first gas and the second gas to the processing system in accordance with a control signal, and using signal means to provide the control signal to the first valve means, in accordance with the composition signal so as to control the flow of the first gas and the second gas as a function of the BTU content of the first gas.

10. A method as described in claim 9 in which the processing system is a hydrogen generation system, the first gas is a hot gas and the second gas is oxygen.

11. A method as described in claim 10 in which the using step uses a NMR means for analyzing the hot gas to provide the first composition signal corresponding thereto.

12. A method as described in claim 11 in which the first providing step includes:

deriving the BTU content of the hot gas from the first composition signal, providing first and second limit signals corresponding to first and second predetermined BTU content limits for the hot gas, and providing the control signal in accordance with the BTU content signal and the first and second limit signals.

13. A method as described in claim 12 in which the controlling step includes controlling the first valve means in accordance with the control signal so as to provide the hot gas and the oxygen to the hydrogen generation system when the BTU content of the hot gas is within the first and second predetermined limits and so as not to provide the hot gas and the oxygen to the hydrogen generation system when the BTU content signal is not within the first and second predetermined limits.

14. A method as described in claim 13 further comprising using second valve means for passing the hot gas to flare or blocking the hot gas in accordance with a second control signal in a manner so that when the hot gas is not being provided to the hydrogen generation system, the hot gas is being flared.

15. A method as described in claim 9 in which the hydrogen generation system provides an off gas including unreacted hydrocarbons; and further comprises the steps of:

analyzing the off gas with second NMR means, and providing a second composition signal corresponding the analysis of the off gas to the signal means, and using third valve means to either provide the off gas back to the hydrogen generation system as a feed gas or to flare the off gas in accordance with the third and fourth control signals.

16. A method as described in claim 15 in which the signal means includes:

second BTU means for deriving the BTU content of the off gas in accordance with the second composition signal, providing a corresponding second BTU content signal in accordance with the derived BTU content of the off gas, providing third and fourth limit signals corresponding to third and fourth predetermined BTU content limits, and providing the third and fourth control signals to the third valve means in accordance with the second BTU content signal and the third and fourth limit signals.

* * * * *